(12) United States Patent
Latikka (10) Patent No.: US 10,307,231 B2
(45) Date of Patent: Jun. 4, 2019

(54) BRUSH HEAD FOR ELECTRIC TOOTHBRUSH

(71) Applicant: Lauri Latikka, Kauniainen (FI)

(72) Inventor: Lauri Latikka, Kauniainen (FI)

(*) Notice: Subject to any disclaimer, the term of this patent is extended or adjusted under 35 U.S.C. 154(b) by 440 days.

(21) Appl. No.: 15/300,325

(22) PCT Filed: Apr. 3, 2015

(86) PCT No.: PCT/FI2015/050236
§ 371 (c)(1),
(2) Date: Sep. 29, 2016

(87) PCT Pub. No.: WO2015/150641
PCT Pub. Date: Oct. 8, 2015

(65) Prior Publication Data
US 2017/0143460 A1 May 25, 2017

(30) Foreign Application Priority Data

Apr. 4, 2014 (EP) .................................. 14163636

(51) Int. Cl.
*A61C 17/34* (2006.01)
*A61C 17/22* (2006.01)

(52) U.S. Cl.
CPC ........ *A61C 17/3436* (2013.01); *A61C 17/222* (2013.01)

(58) Field of Classification Search
CPC ... A61C 17/3436; A61C 17/222; A46B 13/00; A46B 13/001; A46B 13/008; A46B 13/023; A46B 2200/1066
See application file for complete search history.

(56) References Cited

U.S. PATENT DOCUMENTS

| | | | | |
|---|---|---|---|---|
| 4,845,795 A | * | 7/1989 | Crawford | A46B 3/06 15/22.1 |
| 5,226,206 A | * | 7/1993 | Davidovitz | A61C 17/349 15/22.1 |
| 5,577,285 A | * | 11/1996 | Drossler | A61C 17/3436 15/22.1 |
| 6,836,918 B1 | * | 1/2005 | Wong | A61C 17/3436 15/22.1 |

(Continued)

FOREIGN PATENT DOCUMENTS

| | | |
|---|---|---|
| CH | 688537 | 11/1997 |
| WO | WO 9637164 | 11/1996 |

OTHER PUBLICATIONS

International Search Report dated Oct. 8, 2015 for PCT/FI2015/050236.

*Primary Examiner* — Weilun Lo
(74) *Attorney, Agent, or Firm* — Clayton, McKay & Bailey, PC (57) ABSTRACT

The object of the invention is a brush head for an electric toothbrush, the brush head comprising a hollow body part (1), a back and forth rotating shaft (3) inside the body part (1), and a rotating bristle carrier (7) rotated back and forth by the shaft (3) at the first end of the body part (1), and where the second end of the shaft (3) comprises a protrusion (3a) that is in an inclined angle (A) in relation to the rotation axis of the shaft (3). The inclination angle (A) is substantially between 20-70 degrees, and the inclination of the protrusion (3a) is directed towards the rotation axis of the shaft (3).

10 Claims, 5 Drawing Sheets

(56) References Cited

U.S. PATENT DOCUMENTS

| | | | |
|---|---|---|---|
| 2003/0041397 A1 | 3/2003 | Hafemann | |
| 2003/0084525 A1* | 5/2003 | Blaustein | A61C 17/3472 15/22.1 |
| 2003/0221269 A1* | 12/2003 | Zhuan | A61C 17/222 15/28 |
| 2005/0011023 A1* | 1/2005 | Chan | A61C 17/3472 15/22.1 |
| 2005/0022323 A1* | 2/2005 | Chan | A61C 17/222 15/22.1 |
| 2006/0174431 A1* | 8/2006 | Nanda | A61C 17/349 15/22.1 |
| 2007/0251033 A1* | 11/2007 | Brown | A61C 17/349 15/22.1 |
| 2008/0189886 A1* | 8/2008 | Jimenez | A61C 17/349 15/22.4 |
| 2008/0222822 A1* | 9/2008 | Cobabe | A46B 5/0075 15/28 |
| 2011/0016647 A1 | 1/2011 | Biro | |
| 2012/0216831 A1* | 8/2012 | Cobabe | A46B 13/008 134/6 |

* cited by examiner

BRUSH HEAD FOR ELECTRIC TOOTHBRUSH

This application is a United States national phase filing of PCT/FI2015/050236, filed Apr. 3, 2015, which claims priority to EP 14163636.5, filed Apr. 4, 2014, both of which are hereby incorporated by reference herein in their entireties.

The object of the invention is a brush head for an electric toothbrush.

Electric toothbrushes known in prior art contain inside their body parts for example a back and forth rotating plastic actuating shaft, which in turn rotates back and forth a bristle carrier containing a plastic disc equipped with bristles. To the actuating shaft is attached a metallic actuator equipped for example with a metallic spring, which actuator further rotates the aforementioned bristle carrier back and forth based on the reciprocating movement of the actuating shaft. These solutions have a problem that they need to have a great number of components and that for example metallic springs collect dirt and in time lose their effectiveness in which case the whole brush head loses its operational reliability. Furthermore, brush heads in prior art contain a hole for installation on the front side of their body parts, i.e. on the same side with the bristle carrier. In this case a problem is that toothpaste may penetrate through the installation hole inside the body part and cause malfunctions in the operational mechanism of the brush head.

In prior art is also known a brush head of an electric toothbrush as shown in the Swiss patent No. CH688537 A5, in which the upper end of the shaft inside the body part contains a pin, which is placed in a groove in the bristle carrier to rotate the bristle carrier back and forth. The CH patent presents a mechanism whereby the position of the pin can be changed in relation to the rotation axis of the bristle carrier, either towards the rotation axis or away from it. This way, a different rotation angle is obtained to the bristle carrier. In addition, it is mentioned in the CH patent that if the angle of the rotation axis of the bristle carrier is changed, the angle of the pin has to be changed correspondingly. Although, at least two different rotation angles for the bristle carrier are obtained with the solution according to the CH patent, it has, however, not been shown in anyway by the CH patent that by changing just only the angle of the pin an exactly desired rotation angle is obtained for the bristle carrier. Instead, the change of the angle of rotation of the bristle carrier is done by changing the distance of the pin from the rotation axis of the bristle carrier with the help of a difficult and complex mechanism prone to malfunctions.

U.S. Pat. No. 8,302,238 B2 shows a motorized toothbrush tip having a double brush head mechanism rotated by an electric motor through a shaft body that has connected to the brush head mechanism with the help of a dowel like or cylindrical crank member that is inclined at an acute angle in relation to the central axis of the shaft body. In addition the distal end of the crank member is directed towards the central axis of the shaft body. The description of the US patent does not mention the size of the inclination angle AA but according the drawings the angle is about 10 degrees. In the US patent the inclination angle is used to reduce the rotation angle of the second brush head so that when the shaft body rotates 90 degrees the second brush head rotates angle AA as shown in FIG. 19 of the US patent. Thus the rotation angle of the second brush head here is only about ±10 degrees. In addition the groove where the crank member is moving has smooth walls and the groove enlarges towards the bottom of the groove. In that case the edge of the free end of the crank member does not touch the walls of the groove but the contact area is about the middle part of the crank member as can be seen in FIG. 19 of the US patent. One disadvantage in the solution of the US patent is that the second brush head rotates only a little and in order to improve the effectiveness the brush head mechanism has been made very complicated with two brush heads and a gear with teeth between them.

One disadvantage of electric toothbrushes with a vibration effect is that the vibration system is inside the handle. When using that kind of a toothbrush the vibration causes easily numbness to a hand holding the handle tooth brush. For that reason the brushing time may be too short. In addition the vibration mechanism inside the handle is complicated and may cause additional defects.

The object of the present invention is to eliminate the aforementioned drawbacks and to achieve a brush head of an electric tooth brush, which contains minimal possible amount of parts and thus its operating mechanism is very simple, reliable and easy to manufacture in which case also mistakes in manufacturing do not occur. Another object of the present invention is to achieve a brush head of an electric toothbrush where toothpaste cannot penetrate inside the body part of the brush head in which case reliability is better and the brush head is hygienic. And yet another object of the present invention is to achieve a brush head of an electric toothbrush where the vibration mechanism is in the brush head instead of being in the handle of the toothbrush.

The brush head for an electric toothbrush according to the invention has several advantages compared to brush heads of the prior art. One advantage is a structural simplicity that makes the reliability of the brush head possible. In addition a simple structure is easy to manufacture to a well and reliably functioning product, which has no manufacturing defects. One advantage is also the fact that the vibration mechanism is very simple and is situated in the brush head where it does not cause numbness to a hand holding the handle tooth brush. One additional advantage is also the fact that the brush head according to the invention is hygienic because only one assembly hole is needed for assembling the actuating shaft inside the body part of the brush head, and the assembly hole is on the opposing side of the body part compared to the bristle carrier. In that case there is no need for an assembly hole on the side of the bristle carrier, and a danger that toothpaste could penetrate inside the body part during use is small.

In the following, the invention will be described in more detail by the aid of one preferred embodiment with reference to the attached drawings, wherein.

The replaceable brush head for an electric toothbrush according to the invention comprises at least a hollow body part 1 of the brush head, a back and forth rotating actuating shaft 3 inside the body part 1, and a back and forth rotating bristle carrier 7 at the second end of the body part 1. Advantageously, the body part 1, actuating shaft 3 and bristle carrier 7 are made of plastic but as well they can be made also of other suitable materials and their combinations.

Figure 1:
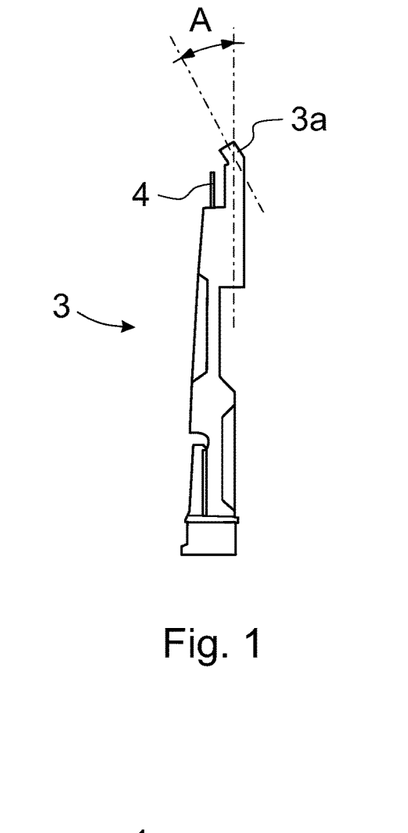
FIG. 1 presents in a side view an actuating shaft according to the invention to be installed inside a body part of the brush head for an electric toothbrush.

FIG. 1 presents in a side view the actuating shaft 3 according to the invention to be installed inside a body part 1 of the brush head. At its second end or the upper end the actuating shaft 3 has a cylindrical pin 4 that is coaxial in relation to the longitudinal rotation axis of the actuating shaft 3. Preferably the pin 4 is made of metal and it acts as an axle pin for the rotation axis of the actuating shaft 3 when the electric motor of the electric toothbrush rotates the actuating shaft 3 back and forth at its first end or lower end. At the side of the pin 4 and the rotation axis of the actuating shaft 3 the second end part of the actuating shaft 3 passes the pin 4 and extends towards the tip of the second end of the actuating shaft 3.

At the tip of the second end of the actuating shaft 3 there is a protrusion 3a acting as a crank member. The protrusion 3a has been inclined with its center axis in an angle A in relation to the rotation axis of the actuating shaft 3. The protrusion 3a is substantially dowel like or cylindrical and is preferably circular in its cross-section but it can also be elliptic in its cross-section, and the protrusion 3a extends in the angle A towards the rotation axis of the actuating shaft 3. Thus the distal end of the protrusion 3a is directed in angle A towards the rotation axis of the actuating shaft 3. Substantially the whole length of the protrusion 3a is of the uniform cross-section. In addition the protrusion 3a is a fixed and integrated part of the actuating shaft 3 and is made of the same material as the actuating shaft 3. Preferably the protrusion 3a has been cast of the same material and at the same time in the same mould as the rest of the actuating shaft 3.

Figure 2:
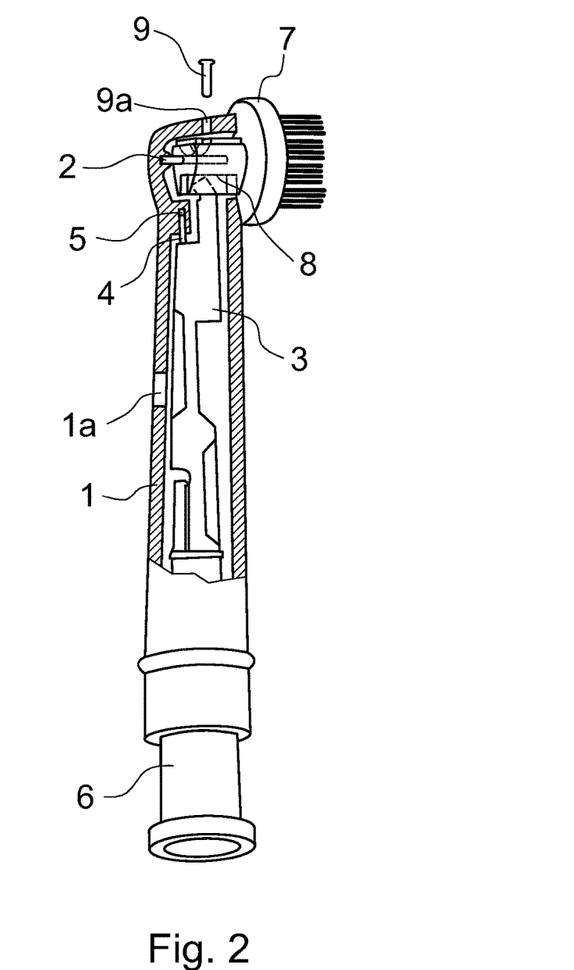
FIG. 2 presents in an oblique side view and partially cross-sectioned a brush head according to the invention, inside which the actuating shaft according to FIG. 1 is installed in its place but where the locking plug is still partially loose.
Figure 3:
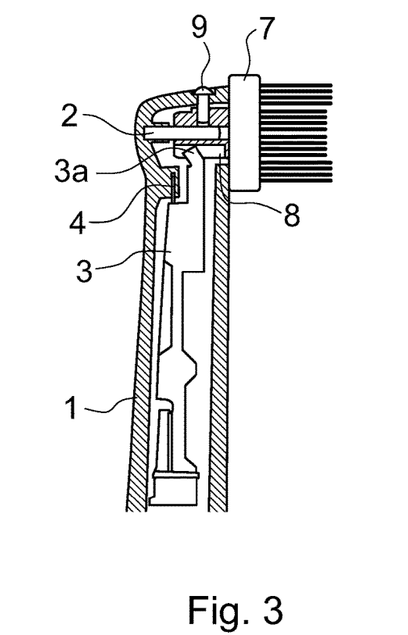
FIG. 3 presents in a side view and partially cross-sectioned an upper end of the brush head according to the invention, inside which the actuating shaft according to FIG. 1 is installed in its place.
Figure 4:
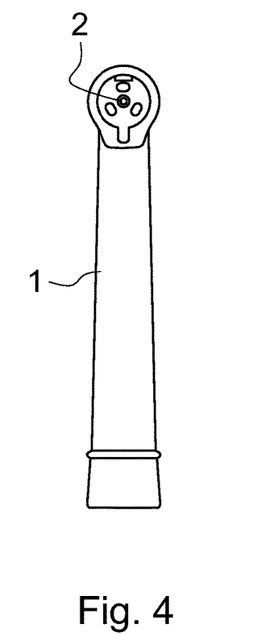
FIG. 4 presents in a front view a brush head according to the invention without a bristle carrier.

FIGS. 2-4 present the brush head according to the invention. The actuating shaft 3 has been installed in its place inside the body part 1 of the brush head, and the bristle carrier 7 has been installed in its place at the second end of the body part 1. The pin 4 is in its place in a hole 5 that is situated near the second end of the body part 1. The pin 4 in the hole 5 keeps the second end of the actuating shaft 3 in its place and allows the actuating shaft 3 rotate back and forth around its rotation axis that is coaxial with the pin 4 and the hole 5. The installation is not yet complete in FIG. 2 because the locking plug 6 aimed to lock the actuating shaft 3 in its place is not yet in its final place inside the first end of the body part 1. The locking plug 6 is also an adapter to connect the brush head model-specifically to the main body of the electric toothbrush, whose primary shaft connects at the same time to the actuating shaft 3 inside the body part 1 of the brush head.

On the backside, i.e. on the opposite side of the body part 1 as the bristle carrier 7 there is an assembly hole 1a in the body part 1 in order to make the assembly of the actuating shaft 3 easier. The assembly hole 1a on the backside of the body part 1 makes it possible that toothpaste does not penetrate inside the body part 1 as easily as in case where the assembly hole would be on the same side of the body part 1 as the bristle carrier 7, or even on both the sides the body part 1.

At the second end of the body part 1 there is a shaft pin 2 that extends from the back wall of the body part 1 towards the bristle carrier 7 and acts as a rotation shaft of the bristle carrier 7. The shaft pin 2 that is preferably made of metal is substantially perpendicular to the rotation axis of the actuating shaft 3 but it can also be in another angle. In addition the bristle carrier 7 has been locked to the second end of the body part 1 with the help of a locking pin 9 that is placed through a locking hole 9a at the second end of the body part 1 to a transversal groove in the body of the bristle carrier 7. The locking pin 9 locks the bristle carrier 7 in its place so that the bristle carrier 7 can rotate back and forth around the shaft pin 2 but the bristle carrier 7 cannot move horizontally along the shaft pin 2 and therefore the bristle carrier 7 cannot disengage from its place.

The back part of the bristle carrier 7 contains a substantially straight groove 8 that is parallel to the rotation axis of the bristle carrier 7. When the bristle carrier 7 is in its place the groove 8 is open substantially towards the second end of the actuating shaft 3 and the protrusion 3a is installed in the groove 8 so that when the actuating shaft 3 is making its back and forth rotation motion around its rotation axis, the protrusion 3a in the groove 8 rotates simultaneously the bristle carrier 7 back and forth. The width of the groove 8 is substantially the same as the width or diameter of the protrusion 3a, or suitably somewhat broader so that the protrusion 3a can be fitted into the groove 8 and can be turned in the groove 8.

Figure 2A:
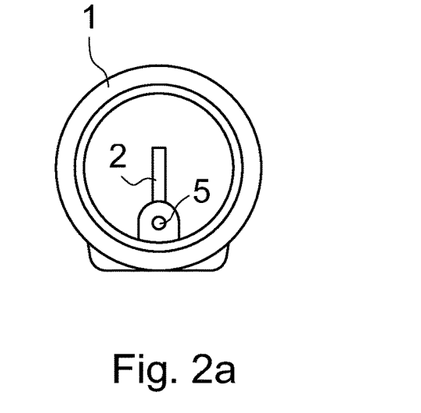
FIG. 2a presents an inner space of the body part of the brush head according to the invention seen from the first end of the body part.

FIG. 2a presents an inner space of the body part 1 of the brush head according to the invention seen from the first end of the body part 1. In FIG. 2a the body part 1 is shown its backside downwards and without the actuating shaft 3 and bristle carrier 7.

Figure 5:
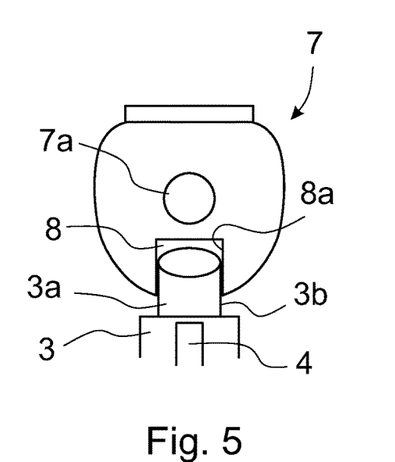
FIG. 5 presents schematically and in a simplified way a bristle carrier according to the invention in its middle position seen from behind.
Figure 6:
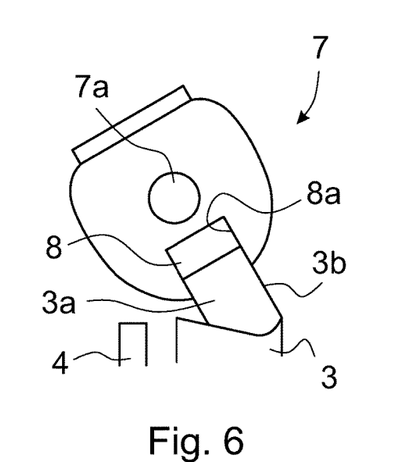
FIG. 6 presents schematically and in a simplified way a bristle carrier according to the invention in its rotated position seen from behind.

FIGS. 5 and 6 present schematically and in a simplified way the bristle carrier 7 according to the invention seen from behind. In FIG. 5 the bristle carrier 7 is in its middle position, and in FIG. 6 the bristle carrier 7 is in its rotated position. Also a part of the second end of the actuating shaft 3 is shown in FIGS. 5 and 6.

The protrusion 3a at the second end of the actuating shaft 3 is arranged into an angle A that is for example 30 degrees in relation to the rotation axis of the actuating shaft 3, and the inclination of the protrusion 3a is directed towards the rotation axis of the actuating shaft 3 so that when the bristle carrier 7 is in the middle position of its rotation area the protrusion 3a is directed obliquely away from the bristle carrier 7 towards the rotation axis of the actuating shaft 3. As mentioned earlier, the rotation axis of the actuating shaft 3 is coaxial with the pin 4. This way the distance of the point of contact between the protrusion 3a and the groove 8 from the rotation axis of the actuating shaft 3 is as short as possible, which improves the durability of the structure and makes at the same time the desired rotation motion possible. The point of contact between the protrusion 3a and the groove 8 is substantially a changing line contact between the sides 8a of the groove 8 and the cylindrical or elliptical envelope surface 3b of the protrusion 3a.

FIGS. 5 and 6 show clearly how the bristle carrier 7 rotates when the actuating shaft 3 rotates around its rotation axis. The bristle carrier 7 has been locked in its place by the shaft pin 2 and the locking pin 9, thus it can only rotate back and forth around the shaft pin 2 that is inserted in the hole 7a. In FIG. 5 the actuating shaft 3 and the bristle carrier 7 are in their middle position. In FIG. 6 the actuating shaft 3 has rotated 90 degrees clockwise from its middle position. When the inclination angle A of the protrusion 3a is for example 30 degrees the protrusion 3a is inclined towards the rotation axis of the actuating shaft 3 and towards the pin 4 the same 30 degrees as is seen in FIG. 6 straight from the side of the actuating shaft 3. The protrusion 3a is in the groove 8 of the bristle carrier 7 and the contact between the envelope surface 3b of the protrusion 3a and the substantially planar sidewalls 8a of the groove 8 is a line contact that has turned the bristle carrier 7 around its rotation axis the same 30 degrees. When the actuating shaft 3 rotates from its middle position counterclockwise the bristle carrier 7 rotates correspondingly to another direction.

In general, it can be noted that the structure of the brush head according to the invention and its components have been dimensioned and arranged so that when the actuating shaft 3 rotates 90 degrees back and forth from its middle position the bristle carrier 7 rotates back and forth from its own middle position an angle that is substantially equal to the inclination angle A of the protrusion 3a.

The actuating shaft 3 can be arranged to rotate back and forth around its rotation axis substantially as many degrees as the primary shaft of the main body of the electric toothbrush rotates back and forth, and in the same phase. Thus, for example, when the primary shaft rotates 30 degrees clockwise the actuating shaft 3 rotates simultaneously the same 30 degrees clockwise, and when the primary shaft rotates degrees counterclockwise the actuating shaft 3 rotates simultaneously the same 30 degrees counterclockwise. In that case the total rotation angle of the actuating shaft 3 is 60 degrees. However, a different transmission ratio can be used to rotate the actuating shaft 3 more or less than the primary shaft rotates.

Also the inclination angle A of the protrusion 3a can be changed. In that case inclination angle A of the protrusion 3a is adjustable and also the rotation angle of the bristle carrier 7 is therefore adjustable. Thus the adjustment of the rotation angle of the bristle carrier 7 has been carried out with the inclination angle A of the protrusion 3a. In that case the inclination angle A of the protrusion 3a can be also smaller or bigger than 30 degrees. It can be for instance between 10-80 degrees, suitably substantially between 20-70 degrees and advantageously between 30-40 degrees, preferably about 30 degrees.

Figure 7:
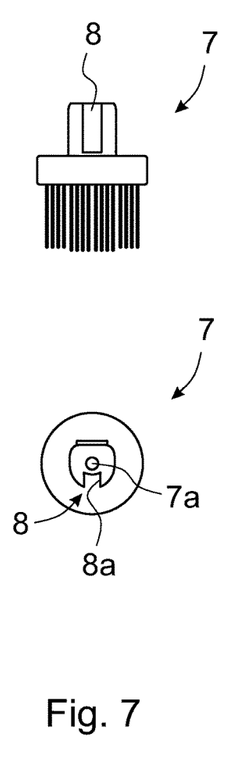
FIG. 7 presents a bristle carrier according to the invention seen from below and behind.
Figure 8:
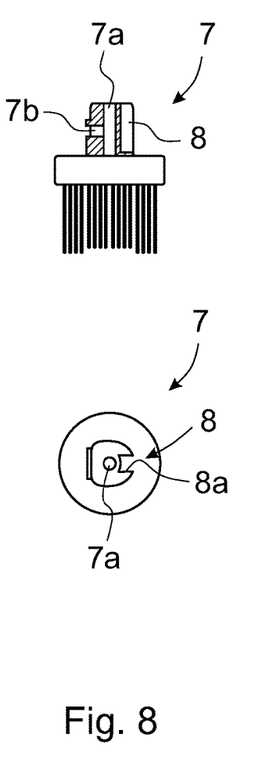
FIG. 8 presents a bristle carrier according to the invention partially cross-sectioned seen from side and behind.
Figure 9:
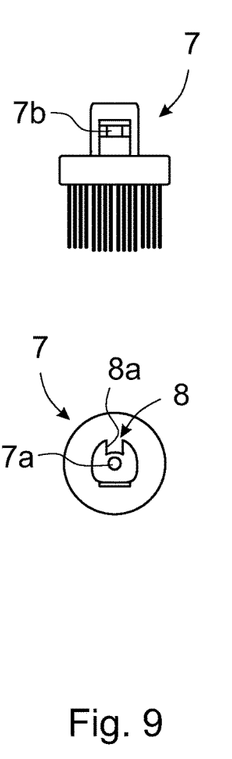
FIG. 9 presents a bristle carrier according to the invention seen from the top and behind.

FIGS. 7-9 present the bristle carrier 7 according to the invention in different positions. FIG. 7 presents the bristle carrier 7 seen from below or from the direction of the handle, and behind whereas FIG. 8 presents the bristle carrier 7 partially cross-sectioned seen from side and behind, and FIG. 9 presents the bristle carrier 7 seen from the top and behind. In its front part the bristle carrier 7 has a group of bristles and in its back part the bristle carrier 7 has a body that comprises the groove 8, the shaft hole 7a and the groove 7b that is transversal in relation to the shaft hole 7a, and is arranged to allow the rotational motion of the bristle carrier 7 when the locking pin 9 is in the groove 7b to prevent the bristle carrier 7 disengaging from the shaft pin 2.

Figure 10:
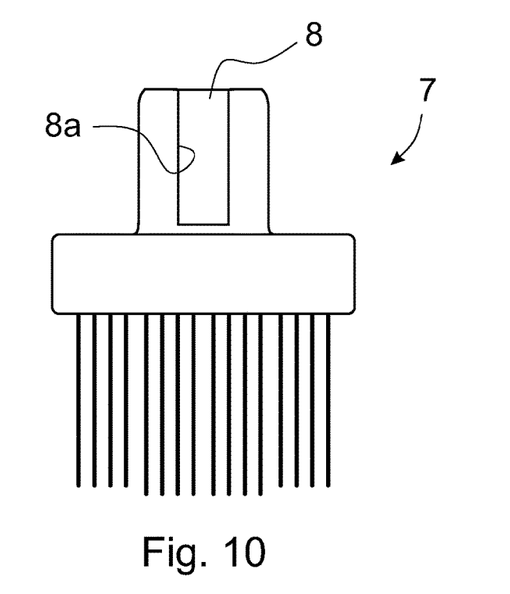
FIG. 10 presents a bristle carrier according to one embodiment of the invention seen from below.
Figure 11:
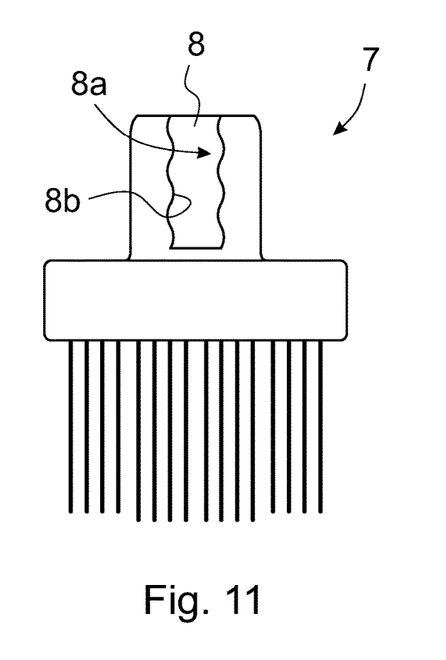
FIG. 11 presents a bristle carrier according to another embodiment of the invention seen from below.
Figure 12:
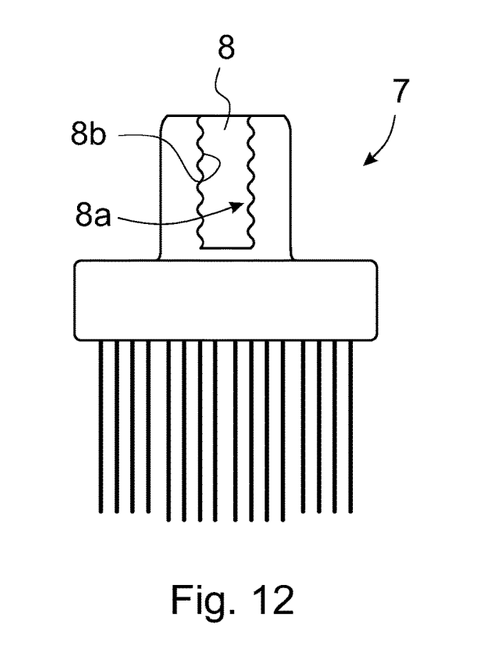
FIG. 12 presents a bristle carrier according to a third embodiment of the invention seen from below.
Figure 13:
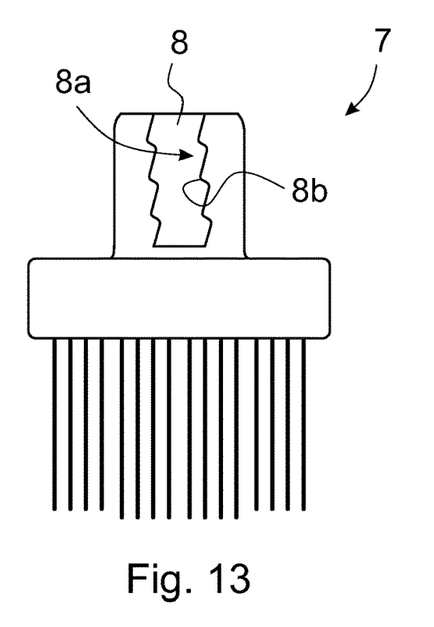
FIG. 13 presents a bristle carrier according to yet another embodiment of the invention seen from below.

Above the bristle carrier 7 with the symmetrical groove 8 having flat and straight sidewalls 8a has been described. That kind of a bristle carrier 7 is described also in FIGS. 7 and 10. The protrusion 3a moves smoothly in the even groove 8 and at the same time rotates the bristle carrier 7 smoothly. In order to make it possible to achieve a rotating and simultaneously vibrating bristle carrier 7 that cleans teeth in a more effective way, another embodiments of the invention are presented in FIGS. 11-15. Instead of being smooth or flat and straight the sidewalls 8a can be uneven having regular or irregular bulges and hollows, which act as guiding means causing the bristle carrier 7 to vibrate during its rotation motion. In that case when seeing the groove 8 perpendicularly towards the rotation axis of the bristle carrier 7 the sidewalls 8a can be, for example, undulated or serrated. FIGS. 11 and 12 show a bristle carrier 7 where the sidewalls 8a of the groove 8 are undulated. Whereas FIGS. 13-15 show a bristle carrier 7 where the sidewalls 8a of the groove 8 are serrated.

The form, direction and size of the undulation and/or serration can vary. In that case the wavelength of the undulation and/or serration can be shorter or longer and the peak-to-peak amplitude of the undulation and/or serration can be smaller or bigger. Also the form of the undulation and/or serration can be symmetrical or asymmetrical. In embodiments shown in FIGS. 11 and 12 the peak-to-peak amplitude of the undulation is essentially the same but the wavelength in FIG. 11 is bigger than in FIG. 12.

Figure 14:
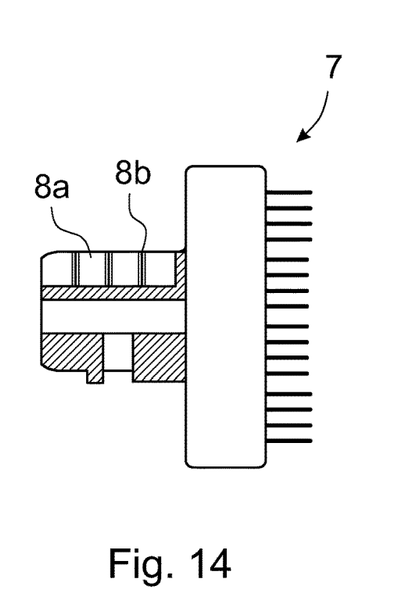
FIG. 14 presents a bristle carrier according to the invention partially cross-sectioned seen from side.
Figure 15:
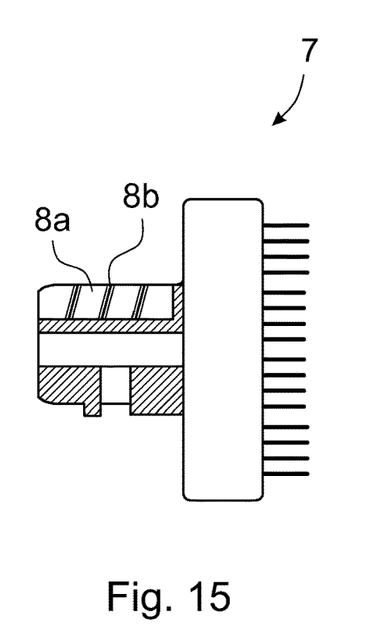
FIG. 15 presents a bristle carrier according to yet another embodiment of the invention seen from side.

In the embodiments shown in FIGS. 11-14 the undulation and serration are straight and the bulges and hollows, for example, wave crests 8b are substantially perpendicular to the bottom of the groove 8. Whereas FIG. 15 presents a structure where the serration is in an inclined position or in an acute angle in relation the bottom of the groove 8. Also the undulation of the sidewalls 8a of the groove 8 can be in an inclined position or in an acute angle in relation the bottom of the groove 8. The wave crest 8b presented in FIGS. 14 and 15 is straight in its entire length but it can also be curvilinear both in undulated sidewalls and serrated sidewalls. The form of the entire wave or serration is similar to the form of its crest.

According to the invention the brush head, more precisely the bristle carrier 7 comprises a guiding means to cause the bristle carrier 7 to vibrate. The intensity or volume of the vibration of bristle carrier 7 is arranged to be adjustable with the help of the form, direction and/or the size of the guiding means comprising the groove 8, its sidewalls 8a and possible undulation or serration on the sidewalls 8a. When the sidewalls 8a are flat and straight the value of the volume of vibration of bristle carrier 7 is zero and vibration does not exist. When the sidewalls 8a are undulated and/or serrated the undulation and/or serration causes vibration to the bristle carrier 7 when the bristle carrier 7 rotates back and forth around its rotation axis.

The adjustment of the vibration of the bristle carrier 7 has been arranged so that the bigger is the amplitude of the undulation or serration the stronger is the volume of the vibration, and the smaller is the wavelength of the undulation or serration the greater is the frequency of the vibration.

Thus the intensity or volume of the vibration of the bristle carrier 7 is arranged to vary between the values 0 and N where 0 means no vibration and N means an amount of vibration, which is a maximum given value, which can be safely used without a danger to cause any harm to the user or to the structure of the toothbrush.

It is obvious to the person skilled in the art that the invention is not limited to the embodiment example presented above, but that it may vary within the scope of the claims to be presented below.

The invention claimed is:

1. A brush head for an electric toothbrush, the brush head comprising:
    a hollow body part having a first end and a second end;
    a back and forth rotating actuating shaft inside the body part;
    a cylindrical pin proximate an end of the actuating shaft, the cylindrical pin is coaxial in relation to the longitudinal rotation axis of the actuating shaft;
    a hole near the second end of the body part, wherein the pin is received in the hole;
    and the body part having a rotating bristle carrier rotated back and forth by the actuating shaft at the second end of the body part,
    wherein the end of the actuating shaft comprises a protrusion that is in an inclined angle (A) in relation to the rotation axis of the actuating shaft,
    wherein the bristle carrier comprises a groove that is substantially straight and parallel to the rotation axis of the bristle carrier, and when the bristle carrier is in its middle position, the groove is open substantially towards the end of the actuating shaft, and the protrusion is inside the groove so that when the actuating shaft is making its back and forth rotation motion around its rotation axis, the protrusion in the groove turns and rotates simultaneously the bristle carrier back and forth, wherein the inclination angle (A) of the protrusion is between 20-70 degrees, and the protrusion is directed to extend towards the rotation axis of the actuating shaft, and that the pin and the inclined protrusion form a combination where the protrusion is extending towards the rotation axis of the actuating shaft and towards the pin.

2. The brush head for an electric toothbrush according to claim 1, wherein the groove has two side walls which are substantially planar, and a mutual distance of the side walls is bigger than the width of the protrusion.

3. The brush head for an electric toothbrush according to claim 2, wherein a contact between the groove and the protrusion is a changing line contact between at least one planar side wall of the groove and an envelope surface of the protrusion.

4. The brush head for an electric toothbrush according to claim 1, wherein the protrusion is circular or elliptic in its cross-section and substantially uniform in its cross-section from its root end to its top end.

5. The brush head for an electric toothbrush according to claim 1, wherein in a middle position of the rotation motion of the actuating shaft, the protrusion is inclined in the angle (A) in a direction towards a back end of the bristle carrier.

6. The brush head for an electric toothbrush according to claim 1, wherein in a middle position of the rotation motion of the actuating shaft, the protrusion has been inclined in the angle (A) in a direction that is parallel to a longitudinal direction of the groove.

7. The brush head for an electric toothbrush according to claim 1, wherein a structure of the brush head and its components have been dimensioned and arranged so that when the actuating shaft rotates 90 degrees back and forth from its middle position, the bristle carrier rotates back and forth from its own middle position an angle that is substantially equal to the inclination angle (A) of the protrusion.

8. The brush head for an electric toothbrush according to claim 1, wherein the inclination angle (A) is between 30 degrees and 40 degrees.

9. The brush head for an electric toothbrush according to claim 1, wherein the protrusion is a fixed and integrated part of the actuating shaft and is made of a same material as the actuating shaft.

10. The brush head for an electric toothbrush according to claim 1, wherein an assembly hole is on an opposite side of the body part compared to the bristle carrier.

* * * * *